(12) United States Patent
Jung et al.

(10) Patent No.: US 11,607,441 B2
(45) Date of Patent: Mar. 21, 2023

(54) PHARMACEUTICAL COMPOSITION FOR PREVENTING OR TREATING DIABETES, CONTAINING ZINC SALT, CYCLO-HISPRO AND ANTIDIABETIC DRUG AS ACTIVE INGREDIENTS

(71) Applicant: NOVMETAPHARMA CO., LTD., Seoul (KR)

(72) Inventors: Hoe Yune Jung, Pohang-si (KR); Jong Su Jeon, Pohang-si (KR); Bo Bae Kim, Seoul (KR); Heon Jong Lee, Incheon (KR); Moon Ki Song, Northridge, CA (US); Do Hyun Lee, Pohang-si (KR)

(73) Assignee: NOVMETAPHARMA CO., LTD., Seoul (KR)

( * ) Notice: Subject to any disclaimer, the term of this patent is extended or adjusted under 35 U.S.C. 154(b) by 0 days.

(21) Appl. No.: 16/757,575

(22) PCT Filed: Oct. 19, 2018

(86) PCT No.: PCT/KR2018/012392
§ 371 (c)(1),
(2) Date: Apr. 20, 2020

(87) PCT Pub. No.: WO2019/078663
PCT Pub. Date: Apr. 25, 2019

(65) Prior Publication Data
US 2020/0353034 A1    Nov. 12, 2020

(30) Foreign Application Priority Data
Oct. 20, 2017    (KR) .......................... 10-2017-0136242

(51) Int. Cl.
| A61K 38/12 | (2006.01) |
| A61P 3/10 | (2006.01) |
| A61K 31/4439 | (2006.01) |
| A61K 31/4985 | (2006.01) |
| A61K 31/7034 | (2006.01) |
| A61K 33/30 | (2006.01) |

(52) U.S. Cl.
CPC .......... *A61K 38/12* (2013.01); *A61K 31/4439* (2013.01); *A61K 31/4985* (2013.01); *A61K 31/7034* (2013.01); *A61K 33/30* (2013.01); *A61P 3/10* (2018.01)

(58) Field of Classification Search
CPC ................ A61K 38/12; A61K 31/4439; A61K 31/4985; A61K 31/7034; A61K 33/30; A61P 3/10
See application file for complete search history.

(56) References Cited

U.S. PATENT DOCUMENTS

| 5,834,032 A * | 11/1998 | Song .............. A61K 31/20 424/641 |
| 2009/0004291 A1* | 1/2009 | Song .............. A61K 45/06 424/641 |
| 2009/0123563 A1 | 5/2009 | Kaarsholm et al. |
| 2013/0053301 A1* | 2/2013 | Rau .................. A61P 37/08 514/1.3 |
| 2015/0202317 A1* | 7/2015 | Rau .................. A61M 5/19 604/92 |

FOREIGN PATENT DOCUMENTS

| KR | 20010022786 | 3/2001 |
| KR | 20060114600 | 11/2006 |
| KR | 20170021926 | 2/2017 |
| WO | WO1999/003477 | 1/1999 |
| WO | WO2007/078726 | 12/2006 |
| WO | WO 2013/095316 | 6/2013 |

OTHER PUBLICATIONS

Cahn et al. Clinical Considerations for Use of Initial Combination Therapy in Type 2 Diabetes. Diabetes Care Aug. 2016, vol. 39, Supplement 2, pp. S137-S145. (Year: 2016).*
Song et al. Metabolic relationships between diabetes and Alzheimer's disease affected by cyclo(his-pro) plus zinc treatment. BBA Clinical (2017) pp. 43-54. (Year: 2017).*
Song. et al. Song et al. Metabolic relationship between diabetes and Alzheimer's Disease affected by Cyclo(His-Pro) plus zinc treatment. BBA Clinical, 2017, 7:41-54 (available online Feb. 10, 2016). (Year: 2017).*
International Search Report and Written Opinion issued in International Patent No. PCT/KR2018/012392, dated Mar. 22, 2019.
Hwang I. K. et al.: "Effects of cyclo (his-pro) plus zinc on glucose metabolism in genetically diabetic obese mice", *Diabetes, Obesity and Metabolism*, vol. 5, No. 5, Sep. 1, 2003, pp. 317-324.
Jung et al.: "Effects of Cyclo-His-Pro-enriched yeast hydrolysate on blood glucose levels and lipid metabolism in obese diabetic ob/ob mice", *Nutrition Research and Practice*, vol. 1. 10, No. 2, Apr. 1, 2016 pp. 154-160.
Luetarian et al. "Handbook of Diabetes Health Education", *Hionan Scientific Press*, Sep. 30, 2017, pp. 137 to 155. (Chinese only. See reference to in corresponding Chinese Office Action, dated Aug. 2, 2021).

(Continued)

*Primary Examiner* — Robert A Wax
*Assistant Examiner* — Olga V. Tcherkasskaya
(74) *Attorney, Agent, or Firm* — Norton Rose Fulbright US LLP

(57) ABSTRACT

The present invention relates to a pharmaceutical composition for preventing or treating diabetes, comprising, as active ingredients: (a) a zinc salt, comprising a zinc cation and anion, and cyclo-hispro, or a pharmaceutically acceptable salt thereof; and (b) an antidiabetic drug (particularly, an insulin sensitizer, an insulin sensitizer, a sodium-glucose co-transporter (a sodium-glucose co-transporter 2 (SGLT2) inhibitor), or a DPP-4 inhibitor).

6 Claims, 7 Drawing Sheets

(56) References Cited

OTHER PUBLICATIONS

Office Action issued in corresponding Chinese Application No. 201880068309.0, dated Aug. 2, 2021. (English Machine Translation).
Song et al.: "Synergistic antidiabetic activities of zinc, cyclo (his-pro), and arachidonic acid" *Metabolism*, Clinical and Experimental, W.B. Saunders Co., Philadelphia, PA, US, vol. 5050, No. 1, Jan. 1, 2001 pp. 53-59.

\* cited by examiner

PHARMACEUTICAL COMPOSITION FOR PREVENTING OR TREATING DIABETES, CONTAINING ZINC SALT, CYCLO-HISPRO AND ANTIDIABETIC DRUG AS ACTIVE INGREDIENTS

CROSS-REFERENCE TO RELATED APPLICATIONS

This application is a national phase application under 35 U.S.C. § 371 of International Application No. PCT/KR2018/012392, filed Oct. 19, 2018, which claims priority to and the benefit of Korean Patent Application No. 10-2017-0136242, filed Oct. 20, 2017. The contents of the referenced patent applications are incorporated into the present application by reference.

FIELD OF THE DISCLOSURE

The present invention relates to a pharmaceutical composition for preventing or treating diabetes, containing a zinc salt, cyclo-hispro and an antidiabetic drug as active ingredients.

DESCRIPTION OF RELATED ART

Diabetes refers to a condition in which insulin, a glucose-regulating hormone secreted from beta cells of the pancreas, cannot be produced in an amount required in the body, or insulin does not act properly on cells, and thus glucose in the blood is accumulated in the blood without being used as energy to induce hyperglycemia, and glucose is detected in urine. Generally, diabetes is divided into insulin-dependent diabetes (type 1 diabetes) and non-insulin-dependent diabetes (type 2 diabetes) depending on whether insulin is essentially required for treatment. Type 2 diabetes is non-insulin-dependent diabetes, which develops because the insulin action is insufficient or insulin is relatively insufficient due to insulin resistance, and 90% of diabetic patients belong to type 2 diabetes, and type 2 diabetes is called adult-type diabetes because it usually develops after their 30 s.

If diabetes persists for a long time, the absorption of glucose in the body does not occur normally, resulting in abnormal carbohydrate metabolism, lipid metabolism, and protein metabolism, so that various diabetic complications such as hyperinsulinemia, neurological complications, diabetic retinopathy (non-proliferative retinopathy, proliferative retinopathy, and diabetic cataracts), renal failure, sexual dysfunction, skin disease (allergy), hypertension, arteriosclerosis, stroke (apoplexy), heart disease (myocardial infarction, angina pectoris, and cardioplegia), and gangrene develop. Accordingly, studies on glucose transport and metabolic processes, the insulin signaling system, and the like have been actively conducted at home and abroad in order to understand the various causes and pathogenesis of type 2 diabetes and make improvement measures, but a drug capable of treating type 2 diabetes fundamentally has not yet been developed.

Thus, the present inventors have come to pay attention to zinc ions as a natural material while having conducted studies on compounds that have excellent antidiabetic activity and can be safely applied.

Antidiabetic studies based on zinc ions have been actively conducted to date, and Korean Patent Application Laid-Open No. 2001-0022786 discloses a compound including zinc ions and cyclo-hispro as a composition useful for reducing diabetes symptoms in mammals, but it has been found that an example of using such a composition in combination with an antidiabetic drug has not been disclosed.

SUMMARY OF THE INVENTION

The present invention has been made in an effort to provide a pharmaceutical composition for preventing or treating diabetes, including: (a) a zinc salt and cyclo-hispro, or a pharmaceutically acceptable salt thereof; and (b) an antidiabetic drug as active ingredients.

However, a technical problem to be achieved by the present invention is not limited to the aforementioned problems, and other problems that are not mentioned may be clearly, understood by a person skilled in the art from the following description.

The present invention provides a pharmaceutical composition for preventing or treating diabetes, including: (a) a zinc salt and cyclo-hispro, or a pharmaceutically acceptable salt thereof; and (b) an antidiabetic drug as active ingredients, in which the antidiabetic drug includes one or more selected from the group consisting of an insulin sensitizer selected from the group consisting of rosiglitazone, troglitazone, ciglitazone, pioglitazone, and englitazone; an insulin secretagogue selected from the group consisting of glybenclamide (glyburide), glipizide, gliclazide, glimepiride, tolazamide, tolbutamide, acetohexamide, carbutamide, chlorpropamide, glibornuride, gliquidone, glipentide, glisolamide, glisoxepide, glyclopyamide, glycylamide, glipentide, repaglinide, and nateglinide; an α-glucosidase inhibitor selected from the group consisting of acarbose, voglibose, emiglitate, and miglitol; a cannabinoid receptor 1 antagonist selected from the group consisting of rimonabant, otenabant, ibinabant, and surinabant; a sodium-glucose co-transporter 2 (SGLT2) inhibitor selected front the group consisting of canagliflozin, dapagliflozin, empagliflozin, ipragliflozin, tofogliflozin, luseogliflozin, remogliflozin, remogliflozin etabonate, and ertugliflozin; a DPP-4 inhibitor selected from the group consisting of sitagliptin, linagliptin, vildagliptin, gemigliptin, saxagliptin, alogliptin, teneligliptin, anagliptin, and evogliptin; and a glucagon-like peptide 1 (GLP1) agonist selected from the group consisting of exenatide, lixisenatide, liraglutide, albiglutide, and dulaglutide.

A weight ratio of the zinc salt and the cyclo-hispro may be 1:20 to 20:1.

A weight ratio of the zinc salt and cyclo-hispro, or a pharmaceutically acceptable salt thereof and the antidiabetic drug may be 3:100 to 30,000:1.

The diabetes may be type 2 diabetes.

The prevention or treatment of diabetes may be caused by the ability to absorb glucose, to lower blood glucose, to regulate blood glucose, or to inhibit the production of glycated hemoglobin.

As an exemplary embodiment of the present invention, a use of (a) a zinc salt and cyclo-hispro, or a pharmaceutically acceptable salt thereof; and (b) an antidiabetic drug for preventing or treating diabetes, in which the antidiabetic drug includes one or more selected from the group consisting of an insulin sensitizer selected from the group consisting of rosiglitazone, troglitazone, ciglitazone, pioglitazone, and englitazone; an insulin secretagogue selected from the group consisting of glybenclamide (glyburide)), glipizide, gliclazide, glimepiride, tolazamide, tolbutamide, acetohexamide, carbutamide, chlorpropamide, glibornuride, gliquidone, glipentide, glisolamide, glisoxepide, glyclopyamide, glycylamide, glipentide, repaglinide, and nateglinide; an α-glucosidase inhibitor selected from the group consisting of acarbose, voglibose, emiglitate, and miglitol; a cannabinoid receptor 1 antagonist selected from the group consisting of rimonabant, otenabant, ibinabant, and surinabant; a sodium-glucose co-transporter 2 (SGLT2) inhibitor selected from the group consisting of canagliflozin, dapagliflozin, empagliflozin, ipragliflozin, tofogliflozin, luseogliflozin, remogliflozin, remogliflozin etabonate, and ertugliflozin; a DPP-4 inhibitor selected from the group consisting of sitagliptin, linagliptin, vildagliptin, gemigliptin, saxagliptin, alogliptin, teneligliptin, anagliptin, and evogliptin; and a glucagon-like peptide 1 (GLP1) agonist selected from the group consisting of exenatide, lixisenatide, liraglutide, albiglutide, and dulaglutide.

As another exemplary embodiment of the present invention, a method for preventing or treating diabetes, the method including: administering (a) a zinc salt and cyclohispro, or a pharmaceutically acceptable salt thereof; and (b) an antidiabetic drug to an individual, in which the antidiabetic drug includes one or more selected from the group consisting of an insulin sensitizer selected from the group consisting of rosiglitazone, troglitazone, ciglitazone, pioglitazone, and englitazone; an insulin secretagogue selected from the group consisting of glybenclamide (glyburide), glipizide, gliclazide, glimepiride, tolazamide, tolbutamide, acetohexamide, carbutamide, chlorpropamide, glibornuride, gliquidone, glipentide, glisolamide, glisoxepide, glyclopyamide, glycylamide, glipentide, repaglinide, and nateglinide; an α-glucosidase inhibitor selected from the group consisting of acarbose, voglibose, emiglitate, and miglitol; a cannabinoid receptor 1 antagonist selected from the group consisting of rimonabant, otenabant, ibinabant, and surinabant; a sodium-glucose co-transporter 2 (SGLT2) inhibitor selected from the group consisting of canagliflozin, dapagliflozin, empagliflozin, tofogliflozin, luseogliflozin, remogliflozin, remogliflozin etabonate, and ertugliflozin; a DPP-4 inhibitor selected from the group consisting of sitagliptin, linagliptin, vildagliptin, gemigliptin, saxagliptin, alogliptin, teneligliptin, anagliptin, and evogliptin; and a glucagon-like peptide 1 (GLP1) agonist selected from the group consisting of exenatide, lixisenatide, liraglutide, albiglutide, and dulaglutide.

A pharmaceutical composition for preventing or treating diabetes according to the present invention includes: a zinc salt and cyclo-hispro, or a pharmaceutically acceptable salt thereof; and (b) an antidiabetic drug as active ingredients, and a combined preparation according to the present invention exhibits a more significant synergistic effect on the ability to absorb glucose, to lower blood glucose, to regulate blood glucose, or to inhibit the production of glycated hemoglobin than a single preparation, so that the combined preparation according to the present invention is expected to be usefully used for preventing or treating type 2 diabetes.

BRIEF DESCRIPTION OF THE DRAWINGS

FIG. 1A is a graph illustrating the results of an oral glucose tolerance test (OGTT) for KKay mice administered Cyclo-Z (zinc salt and cyclo-hispro), confirming the effect on a change in blood glucose over time after glucose administration. FIG. 1B illustrates the blood glucose values of KKay mice administered Cyclo-Z (zinc salt and cyclo-hispro) over the passage of 2 hours after glucose administration as the area under the glucose curve.

FIGS. 4A and 4B illustrate the blood glucose values of KKay mice administered a combined preparation or single preparation of Cyclo-Z (zinc salt and cyclo-hispro) and dapagliflozin over the passage of 2 hours after glucose administration as the area under the glucose curve, and the comparison of the blood glucose values. FIGS. 4C and 4D illustrate the comparison of measured glycated hemoglobin of each of KKay mice administered a combined preparation or single preparation of Cyclo-Z (zinc salt and cyclo-hispro) and dapagliflozin.

FIG. 5A illustrates the blood glucose values of KKay mice administered a combined preparation or single preparation of Cyclo-Z (zinc salt and cyclo-hispro) and metformin over the passage of 2 hours after glucose administration as the area under the glucose curve, and the comparison of the blood glucose values. FIG. 5B illustrates the comparison of measured glycated hemoglobin of each of KKay mice administered Cyclo-Z (zinc salt and cyclo-hispro) and metformin.

DETAILED DESCRIPTION OF THE INVENTION

Figure 1A:
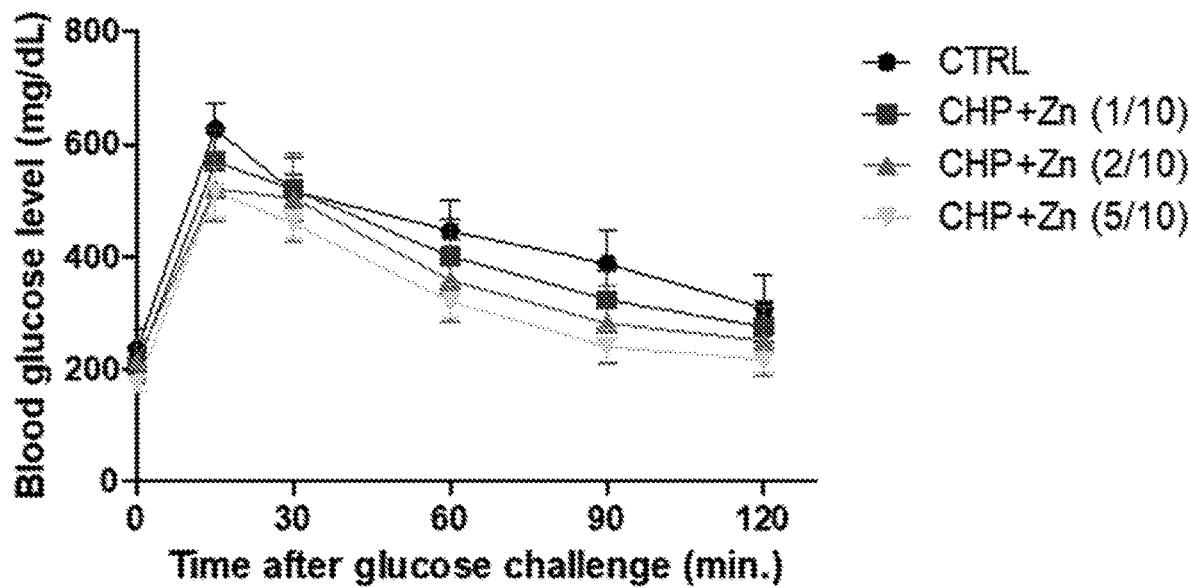
FIGS. 1A and 1B.

The present inventors prepared a combined preparation by mixing a antidiabetic drug with Cyclo-Z (zinc salt and cyclo-hispro) or a pharmaceutically acceptable salt thereof, and confirmed that the combined preparation exhibited a more significant synergistic effect on the ability to absorb glucose, to lower blood glucose, to regulate blood glucose, or to inhibit the production of glycated hemoglobin than a single preparation and could prevent or treat type 2-diabetes effectively, thereby completing the present invention.

An exemplary embodiment of the present invention confirmed a synergistic effect on the ability to absorb glucose according to the treatment with a combined preparation of Cyclo-Z (zinc salt and cyclo-hispro) and rosiglitazone (see Example 2).

Another exemplary embodiment of the present invention confirmed a synergistic effect on the ability to lower blood glucose or to regulate blood glucose according to the treatment with a combined preparation of Cyclo-Z (zinc salt and cyclo-hispro) and sitagliptin (see Example 3).

Still another exemplary embodiment of the present invention confirmed a synergistic effect on the ability to lower blood glucose, to regulate blood glucose, or to inhibit the production of glycated hemoglobin according to the treatment with a combined preparation of Cyclo-Z (zinc salt and cyclo-hispro) and sitagliptin (see Example 4).

Accordingly, the present invention includes: (a) a zinc salt and cyclo-hispro, or a pharmaceutically acceptable salt thereof; and
(b) an antidiabetic drug, as active ingredients,
in which the antidiabetic drug may be used as a pharmaceutical composition for preventing or treating diabetes, including: (a) a zinc salt and cyclo-hispro, or a pharmaceutically acceptable salt thereof; and (b) an antidiabetic drug as active ingredients, in which the antidiabetic drug includes one or more selected from the group consisting of an insulin sensitizer selected from the group consisting of rosiglitazone, troglitazone, ciglitazone, pioglitazone, and englitazone; an insulin secretagogue selected from the group consisting of glybenclamide (glyburide), glipizide, gliclazide, glimepiride, tolazamide, tolbutamide, acetohexamide, carbutamide, chlorpropamide, glibornuride, gliquidone, glipentide, glisolamide, glisoxepide, glyclopyamide, glycylamide, glipentide, repaglinide, and nateglinide; an α-glucosidase inhibitor selected from the group consisting of acarbose, voglibose, emiglitate, and miglitol; a cannabinoid receptor 1 antagonist selected from the group consisting of rimonabant, otenabant, ibinabant, and surinabant; a sodium-glucose co-transporter 2 (SGLT2) inhibitor selected from the group consisting of canagliflozin, dapagliflozin, empagliflozin, ipragliflozin tofogliflozin, luseogliflozin, remogliflozin, remogliflozin etabonate, and ertugliflozin; a DPP-4 inhibitor selected from the group consisting of sitagliptin, linagliptin, vildagliptin, gemigliptin, saxagliptin, alogliptin, teneligliptin, anagliptin, and evogliptin; and a glucagon-like peptide 1 (GLP1) agonist selected from the group consisting of exenatide, lixisenatide, liraglutide, albiglutide, and dulaglutide.

The composition is for preventing or treating diabetes, particularly, type-2 diabetes, and the prevention or treatment of diabetes may be caused by the ability to absorb glucose, to lower blood glucose, to regulate blood glucose, or to inhibit the production of glycated hemoglobin. The composition may have an advantage of being capable of alleviating side effects such as fractures, body weight gain, renal dysfunction, and diarrhea caused by the antidiabetic drug.

First, the pharmaceutical composition for preventing or treating diabetes according to the present invention includes (a) a zinc salt and cyclo-hispro, or a pharmaceutically acceptable salt thereof.

Specifically, the zinc salt includes zinc cations and anions, and in this case, a chloride, a sulfate, or the like may be used as the anion. Since insulin resistance appears when zinc present at high concentration in beta cells of the pancreas is deficient, the zinc salt is intended to eliminate such zinc deficiency.

Meanwhile, the cyclo-hispro is an enzyme which promotes zinc and zinc metabolism, and in this case, as the cyclo-hispro, purified cyclo-hispro may be used.

Accordingly, the zinc salt and cyclo-hispro is also referred to as "Cyclo-Z", and may improve insulin resistance by promoting the synthesis of an insulin-degrading enzyme (IDE) and increasing the degree of activity.

A weight ratio of the zinc salt and the cyclo-hispro may be 1:20 to 20:1, and is preferably 1:1, and more preferably 1:1 to 3:1, but is not limited thereto.

Next, the pharmaceutical composition for preventing or treating diabetes according to the present invention further includes (b) an antidiabetic drug.

Specifically, the antidiabetic drug is a drug which is currently under development at the clinical stage, and the like or commercially available, and specifically, the antidiabetic drug may be a composition containing an insulin sensitizer, an insulin secretagogue, an α-glucosidase inhibitor, a cannabinoid receptor 1 antagonist, a DPP-4 inhibitor, a glucagon-like peptide 1 (GLP1) agonist, and a sodium-glucose co-transporter 2 (SGLT2) inhibitor, and is preferably an insulin sensitizer, a sodium-glucose co-transporter 2 (SGLT2) inhibitor, or a. DPP-4 inhibitor, but is not limited thereto.

More specifically, the insulin sensitizer may be selected from the group consisting of rosiglitazone, troglitazone, ciglitazone, pioglitazone, and englitazone; the insulin secretagogue may be selected from the group consisting of glybenclamide (glyburide), glipizide, gliclazide, glimepiride, tolazamide, tolbutamide, acetohexamide, carbutamide, chlorpropamide, glibornuride, gliquidone, glisentide, glisolamide, glisoxepide, glyclopyamide, glycylamide, glipentide, repaglinide, and nateglinide, the α-glucosidase inhibitor may be selected from the group consisting of acarbose, voglibose, emiglitate, and miglitol); the cannabinoid receptor 1 antagonist may be selected from the group consisting of rimonabant, otenabant, ibinabant, and surinabant; the sodium-glucose co-transporter 2 (SGLT2) inhibitor may be selected from the group consisting of canagliflozin, dapagliflozin, empagliflozin, ipragliflozin, tofogliflozin, luseogliflozin, remogliflozin, remogliflozin, and ertugliflozin; the dipeptidyl peptidase 4 (DPP-4) inhibitor may be selected from the group consisting of sitagliptin, linagliptin, vildagliptin, gemigliptin, saxagliptin, alogliptin, teneligliptin, anagliptin, and evogliptin; and the glucagon-like peptide 1 (GLP1) agonist may be selected from the group consisting of exenatide, lixisenatide, liraglutide, albiglutide, and dulaglutide.

Even when Cyclo-Z (zinc salt and cyclo-hispro), or a pharmaceutically acceptable salt thereof is used as a single preparation, or an antidiabetic drug such as an insulin sensitizer such as rosiglitazone; a sodium-glucose co-transporter 2 (SGLT2) inhibitor such as dapagliflozin; or a DPP-4 inhibitor such as sitagliptin is used as a single preparation, an effect such as the regulation of blood glucose is exhibited to some degree, but is at an insignificant level. However, a combined preparation for these may have a significant synergistic effect on the regulation of blood glucose, and the like. On the other hand, when metformin, which is a type of biguanide drug, is used as the antidiabetic drug, a synergistic effect on the ability to regulate blood glucose or inhibit the production of glycated hemoglobin according to the treatment with a combined preparation of Cyclo-Z (zinc salt and cyclo-hispro) and metformin is not confirmed.

A weight ratio of the Cyclo-Z (zinc salt and cyclo-hispro), or the pharmaceutically acceptable salt thereof and the antidiabetic drug is preferably 3:100 to 30,000:1, more preferably 3:100 to 30:1, and even more preferably 3:100 to 6:1, but is not limited thereto. In this case, when the proportion of the Cyclo-Z (zinc salt and cyclo-hispro), or the pharmaceutically acceptable salt thereof is much larger than that of the antidiabetic drug, there is a problem in that the effect of regulating blood glucose or inhibiting glycated hemoglobin deteriorates.

As used herein, the term "treatment" refers to all actions that ameliorate or beneficially change symptoms of diabetes by administering the pharmaceutical composition according to the present invention.

Thus, the Cyclo-Z (zinc salt and cyclo-hispro), or the pharmaceutically acceptable salt thereof and the antidiabetic drug may further include an appropriate carrier, an appropriate excipient, and an appropriate diluent, which are typically used to prepare a pharmaceutical composition. Further, the pharmaceutical composition may be used by being formulated in the form of an oral formulation such as a powder, a granule, a tablet, a capsule, a suspension, an emulsion, a syrup, and an aerosol, an external preparation, a suppository, and a sterile injection solution, according to a typical method.

Examples of the carrier, the excipient, and the diluent, which may be included in the composition include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, and the like. When the composition is prepared, the composition is prepared using a commonly used diluent or excipient, such as a filler, an extender, a binder, a wetting agent, a disintegrant, and a surfactant.

The pharmaceutical composition according to the present invention is administered in a pharmaceutically effective amount. As used herein, the "pharmaceutically effective amount" refers to an amount sufficient to treat diseases at a reasonable benefit/risk ratio applicable to medical treatment, and an effective dosage level may be determined according to factors including types of diseases of patients, the severity of disease, the activity of drugs, sensitivity to drugs, administration time, administration route, excretion rate, treatment period, and simultaneously used drugs, and other factors well known in the medical field.

The pharmaceutical composition according to the present invention may be preferably administered simultaneously, separately or sequentially with a drug to be used in combination, and may be administered once or multiple times, in order to enhance the therapeutic effect. It is important to administer the composition in a minimum amount that can obtain the maximum effect without any side effects, in consideration of all the aforementioned factors, and this amount may be easily determined by the person skilled in the art. Specifically, the effective amount of the pharmaceutical composition according to the present invention may, vary depending on the age, sex, condition, and body weight of a patient, the absorption rate, inactivation rate and excretion rate of the active ingredient in vivo, the type of the disease, and the drug to be used in combination.

The pharmaceutical composition of the present invention may be administered to an individual via various routes. All modes of administration may be expected, and it may be administered, for example, by oral administration, intranasal administration, transtracheal administration, arterial injection, intravenous injection, subcutaneous injection, intramuscular injection, or intraperitoneal injection.

The pharmaceutical composition of the present invention is determined by the type of drug that is an active ingredient, as well as various related factors such as the disease to be treated, the route of administration, the age, sex, and body weight of a patient, and the severity of the disease.

As used herein, the "individual" refers to a subject in need of treatment of a disease, and more specifically, refers to a mammal such as a human or a non-human primate, a mouse, a rat, a dog, a cat, a horse, and a cow.

The present invention is a use of (a) a zinc salt and cyclo-hispro, or a pharmaceutically acceptable salt thereof; and (b) an antidiabetic drug for preventing or treating diabetes, in which the antidiabetic drug includes one or more selected from the group consisting of an insulin sensitizer selected from the group consisting of rosiglitazone, troglitazone, ciglitazone, pioglitazone, and englitazone; an insulin secretagogue selected from the group consisting of glybenclamide (glyburide), glipizide, gliclazide, glimepiride, tolazamide, tolbutamide, acetohexamide, carbutamide, chlorpropamide, glibornuride, gliquidone, glisentide, glisolamide, glisoxepide, glyclopyamide, glycylamide, glipentide, repaglinide, and nateglinide; an α-glucosidase inhibitor selected from the group consisting of acarbose, voglibose, emiglitate, and miglitol; a cannabinoid receptor 1 antagonist selected from the group consisting of rimonabant, otenabant, ibinabant, and surinabant; a sodium-glucose co-transporter 2 (SGLT2) inhibitor selected from the group consisting of canagliflozin, dapagliflozin, empagliflozin, ipragliflozin, tofogliflozin, luseogliflozin, remogliflozin, remogliflozin etabonate, and ertugliflozin; a DPP-4 inhibitor selected from the group consisting of sitagliptin, linagliptin, vildagliptin, gemigliptin, saxagliptin, alogliptin, teneligliptin, anagliptin, and evogliptin; and a glucagon-like peptide 1 (GLP1) agonist selected from the group consisting of exenatide, lixisenatide, liraglutide, albiglutide, and dulaglutide.

Further, the present invention is a method for preventing or treating diabetes, the method including: administering (a) a zinc salt and cyclo-hispro, or a pharmaceutically acceptable salt thereof; and (b) an antidiabetic drug to an individual, in which the antidiabetic drug includes one or more selected from the group consisting of an insulin sensitizer selected from the group consisting of rosiglitazone, troglitazone, ciglitazone, pioglitazone, and englitazone; an insulin secretagogue selected from the group consisting of glybenclamide (glyburide), glipizide, gliclazide, glimepiride, tolazamide, tolbutamide, acetohexamide, carbutamide, chlorpropamide, glibornuride, gliquidone, glisentide, glisolamide, glisoxepide, glyclopyamide, glycylamide, glipentide, repaglinide, and nateglinide; an α-glucosidase inhibitor selected from the group consisting of acarbose, voglibose, emiglitate, and miglitol; a cannabinoid receptor 1 antagonist selected from the group consisting of rimonabant, otenabant, ibinabant, and surinabant; a sodium-glucose co-transporter 2 (SGLT2) inhibitor selected from the group consisting of canagliflozin, dapagliflozin, empagliflozin, ipragliflozin, tofogliflozin, luseogliflozin, remogliflozin, remogliflozin etabonate, and ertugliflozin; a DPP-4 inhibitor selected from the group consisting of sitagliptin, linagliptin, vildagliptin, gemigliptin, saxagliptin, alogliptin, teneligliptin, anagliptin, and evogliptin; and a glucagon-like peptide 1 (GLP1) agonist selected from the group consisting of exenatide, lixisenatide, liraglutide, albiglutide, and dulaglutide.

Hereinafter, preferred Examples for helping the understanding of the present invention will be suggested. However, the following Examples are provided only to more easily understand the present invention, and the contents of the present invention are not limited by the following Examples.

Preparation Example

A zinc salt, cyclo-hispro, and rosiglitazone used in the following Examples was purchased from Captek Softgel International, purchased from Bachem Holding AG, and purchased from TCI Co., Ltd., respectively, and used.

EXAMPLES

Example 1. Measurement of Blood Glucose Regulation Effect in Mice by Cyclo-Z (Zinc Salt and Cyclo-Hispro)

1-1. Administration of Cyclo-Z and Negative Control 5-week-old KKAy mice purchased from Saeronbio Inc. were preliminarily reared 1 week, and then divided into 4 groups of 5 animals each.

Group 1 was set as a negative control by administration of phosphate buffered saline, and Group 2, Group 3, and Group 4 were orally administered a zinc salt and cyclo-hispro daily at a weight ratio of 10:1, 10:2, and 10:5, respectively, for 8 weeks.

1-2. Measurement of Oral Glucose Load Test in Mice

In order to confirm the effect of regulating blood glucose, the animals in the control and the experimental groups were orally administered 2 g/kg of glucose after fasting for 6 hours, and the blood glucose level was measured at 30 minute intervals for 2 hours. An oral glucose tolerance test (OGTT) was used to measure the blood glucose level. For the experimental results, the significance thereof was verified by performing t-tests on those within 33% of the average of each of the experimental groups and the control, and a statistically significant difference was shown (*$p<0.05$).

Figure 1B:
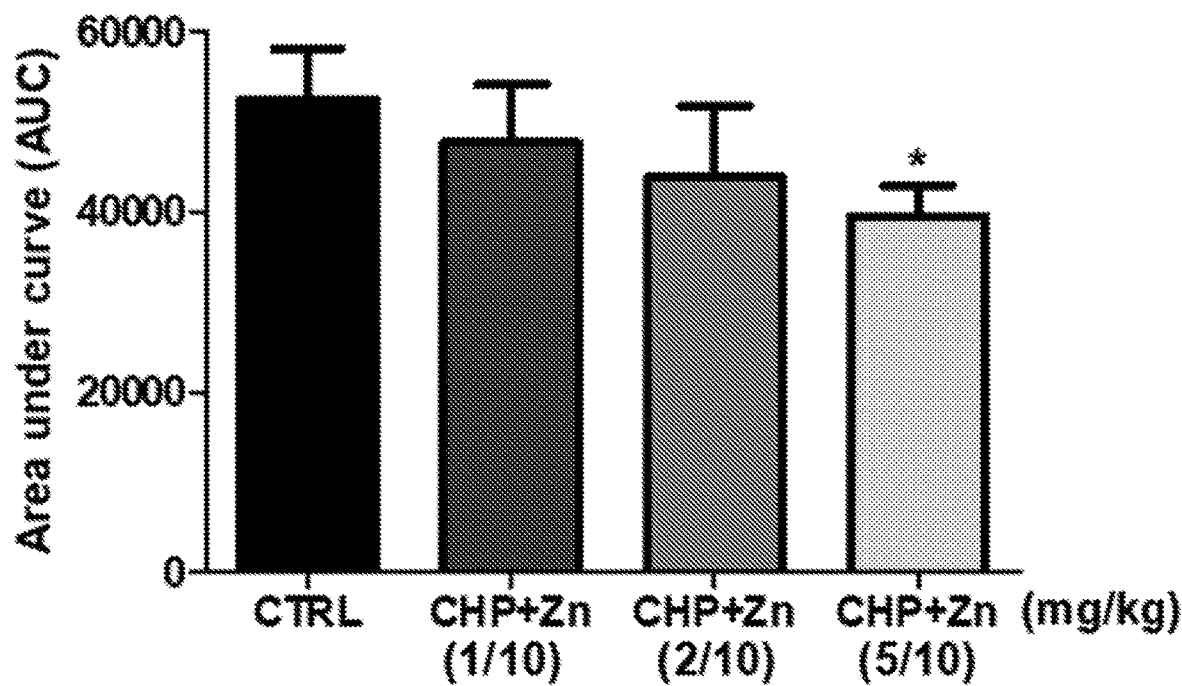

As a result, as illustrated in FIGS. 1A and 1B, it was confirmed that blood glucose was rapidly reduced 2 hours after glucose administration in the group administered a zinc salt and cyclo-hispro at a weight ratio of 10:5, compared to the control. Specifically, the blood glucose of the control group 2 hours after the glucose loading was 308.5 mg/dl, whereas the blood glucose of the group to which the zinc salt and cyclo-hispro were administered at a weight ratio of 10:5 was 217.5 mg/dl. Therefore, it could be confirmed that the weight ratio of the zinc salt and the cyclo-hispro of 10:5 was the most ideal combination.

Example 2. Measurement of Glucose Uptake Effect in Adipocytes According to Administration of Combined Preparation of Cyclo-Z (Zinc Salt and Cyclo-Hispro) and Rosiglitazone In muscle, fat, liver cells, and the like, the signaling by insulin causes phosphorylation of the insulin receptor, and accordingly, when various downstream proteins are phosphorylated, the ability to absorb glucose is increased, thereby lowering blood glucose. Accordingly, in order to confirm whether the combined preparation of Cyclo-Z and rosiglitazone is effective for diabetes, an experiment for evaluating the ability to absorb glucose was performed. Undifferentiated 3T3-L1 cells as adipocytes were cultured in a DMEM containing 10% fetal bovine serum (FBS). After being cultured for 48 hours, in order to differentiate into adipocytes, the undifferentiated 3T3-L1 cells were cultured in a DMEM including 10% FBS, 0.05 M of isobutylmethylxanthine, 1 μM of dexamethasone, and 1 μg/ml of insulin for 48 hours, and cultured in a DMEM including 10% of PBS, and 1 μg/ml of insulin for 96 hours by replacing the culture solution every 48 hours. Finally, after differentiation by culturing the undifferentiated 3T3-L1 cells in a DMEM including 10% FBS, insulin resistance was induced by a DMEM including 10 nmol of insulin. Thereafter, each sample was treated with a glucose-free DMEM including 5.72 μg/ml of a zinc salt, 0.572 μg/ml of cyclo-hispro, and 50 μM of rosiglitazone for 3 hours, and stimulated with 100 nmol of insulin for the final 15 min. The subsequent experimental procedure was performed according to the protocol provided in a glucose uptake cell-based assay kit (600470, Cayman). After insulin stimulation, the sample was washed with phosphate buffered saline, diluted with a provided 2-NBDG glucose free DMEM to 200 μg/ml, and treated for 30 minutes. After the culture solution was removed, fluorescence was measured using Infinite® 200 PRO (TECAN). For the experimental results, the significance thereof was verified by performing a comparative verification between an experimental group in an insulin-resistant state and each control, between an experimental group in a normal state and an insulin-treated control in a normal state, between a Cyclo-Z single or rosiglitazone single experimental group in an insulin-resistant state and an experimental group treated with a combined preparation of Cyclo-Z and rosiglitazone using a t-test, and the experimental results exhibited a statistically significant difference (*$p<0.05$, $p<0.005$, *$p<0.0005$, #$p<0.05$, ##$p<0.005$).

Figure 2:
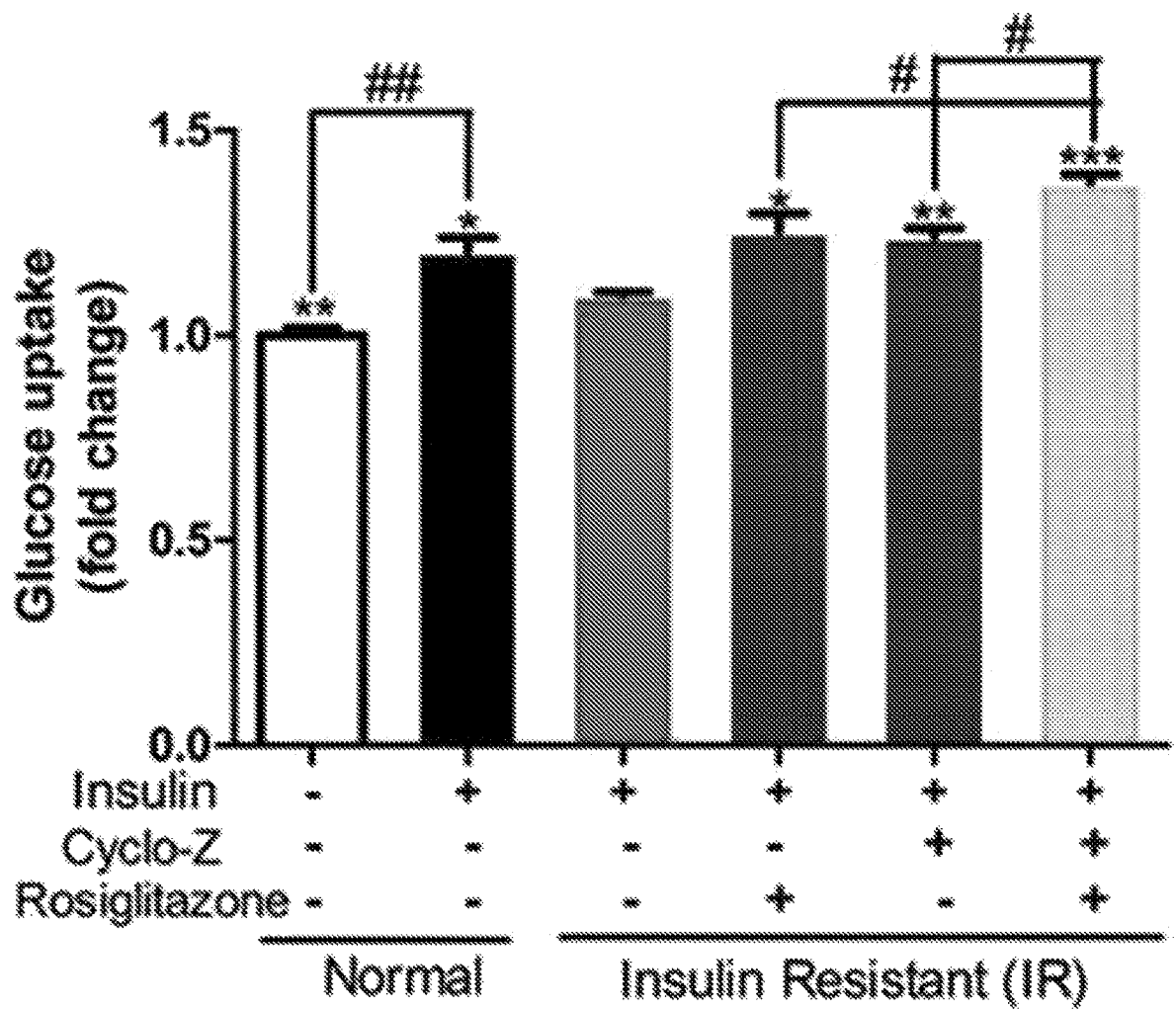
FIG. 2 is a graph illustrating the measurement of absorption values of glucose analogs when 3T3-L1 adipocyte cell lines, which are mouse-derived adipocytes are treated with a combined preparation of Cyclo-Z (zinc salt and cyclo-hispro) and rosiglitazone was treated for 3 hours.

As a result, as illustrated in FIG. 2, glucose absorption was significantly increased during treatment with insulin in a normal state, whereas glucose absorption was not significantly increased in spite of treatment with insulin, whereas a greater synergistic effect was confirmed in the treatment with a combined preparation of Cyclo-Z and rosiglitazone than in Cyclo-Z single or rosiglitazone single treatment. Therefore, it could be seen that the treatment with a combined preparation of Cyclo-Z and rosiglitazone could be used for treating a related disease, type-2 diabetes, by confirming that the treatment had a positive effect on the regulation of blood glucose and the improvement of glucose metabolism through an increase in glucose absorption in adipocytes in an insulin-resistant state.

Example 3. Measurement of Blood Glucose Lowering and Blood Glucose Regulation Effects in Mice by Administration of Cyclo-Z (Zinc Salt and Cyclo-Hispro) and Sitagliptin 3-1. Administration of Single and Combined Preparations of Cyclo-Z and Sitagliptin In order to measure the effects of regulating blood glucose by the combined preparation of Cyclo-Z and sitagliptin, 6-week-old KKAy mice were purchased from CLEA Japan, Inc. and reared under predetermined conditions (temperature: 22±2° C., relative humidity: 55±10%, daily cycle: 12 hours). 7 animals were grouped, water and food were freely supplied in cages, and the groups were subjected to acclimatization for 1 week before the experiment and used for the experiment.

After the acclimatization period, the animals were divided into 4 groups, and sin and combined preparations of Cyclo-Z and sitagliptin at weight ratios shown in the following Table 1 were orally administered daily for 8 weeks.

TABLE 1

| Group | Cyclo-Z | Sitagliptin |
|---|---|---|
| Normal control | — | — |
| Single administration group | 3 | — |
|  | — | 1 |
|  | — | 2 |
| Cyclo-Z:Sitagliptin complex composition administration group | 3 | 1 |
|  | 3 | 2 |

5-week-old KKAy mice purchased from Saeronbio Inc. were preliminarily reared for 1 week, and then divided into 4 groups of 8 animals each.

Group 1 was set as a negative control by administration of phosphate buffered saline, and Group 2, Groups 3 and 4, and Groups 5 and 6 as a Cyclo-Z administration group, sitagliptin administration groups, and complex composition administration groups of a complex composition of Cyclo-Z and sitagliptin at weight ratios of 3:1 and 3:2, respectively, were orally administered daily for 17 weeks.

3-2. Measurement of Oral Glucose Load Test in Mice

In order to confirm the effect of regulating blood glucose, the animals in the control and the experimental groups were orally administered 2 g/kg of glucose after fasting for 16 hours, and the blood glucose level was measured at 15, 30, 60, 90, and 120 minutes. An oral glucose tolerance test (OGTT) was used to measure the blood glucose level. For the experimental results, the significance thereof was verified by performing a t-test between the negative control and the experimental groups, and the experimental results exhibited a statistically significant difference ($p<0.01$, *$p<0.001$, ****$p<0.0001$). Further, the significance thereof was verified by performing a t-test between the single administration group and the complex administration group, and the experimental results exhibited a significant difference (#$p<0.05$, ###$p<0.001$).

Figure 3A:
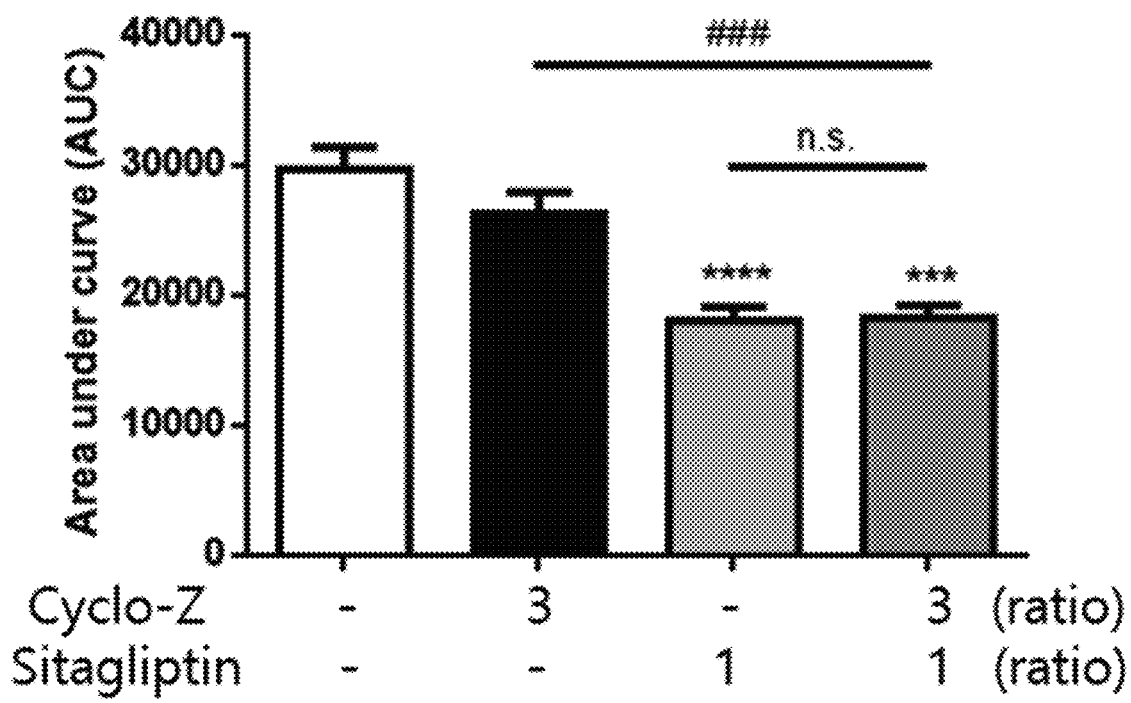
FIGS. 3A and 3B illustrate the blood glucose values of KKay mice administered a combined preparation or single preparation of Cyclo-Z (zinc salt and cyclo-hispro) and sitagliptin over the passage of 2 hours after glucose administration as the area under the glucose curve, and the comparison of the blood glucose values.
Figure 3B:
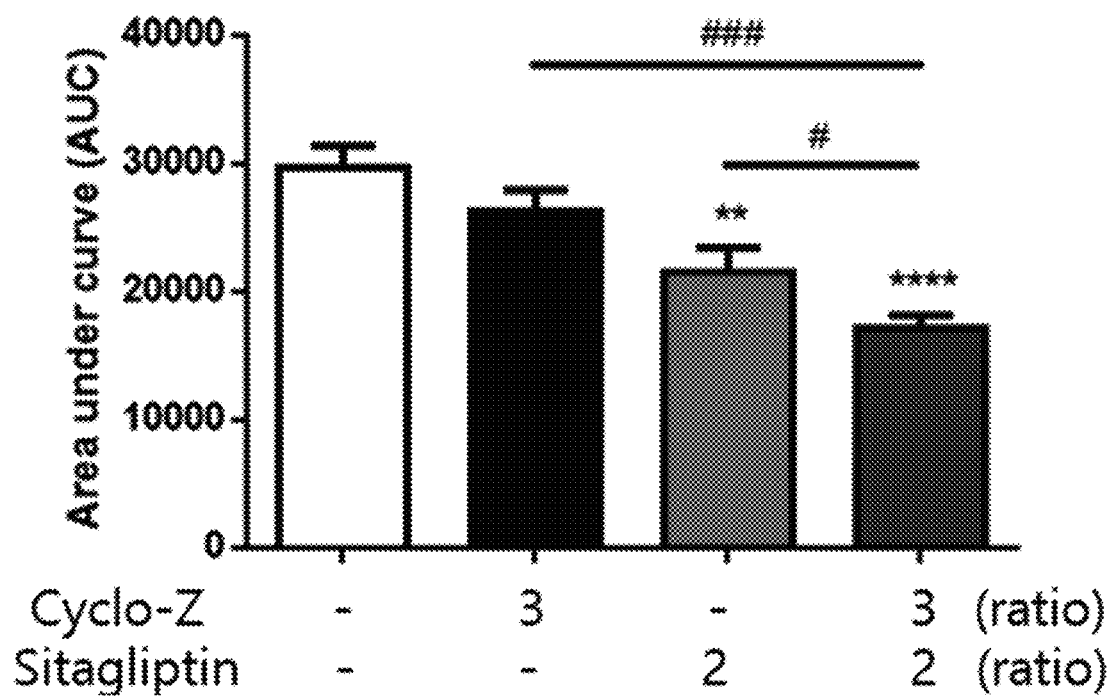

As a result, as illustrated in FIGS. 3A and 3B, it was confirmed that blood glucose was rapidly reduced 2 hours after glucose administration in the complex administration group in which Cyclo-Z and sitagliptin were administered at a weight ratio of 3:2 rather than at a weight ratio of 3:1, compared to the single administration group.

Therefore, since an excellent significant action of reducing the concentration of blood glucose in the combined preparation administration group rather than the case of the Cyclo-Z single or sitagliptin single administration group was confirmed, it could be seen that the combined preparation in which Cyclo-Z and sitagliptin were administered at a weight ratio of 3:2 could be usefully used for preventing or treating diabetes, and it could be seen that the combined preparation could be usefully used as an agent for preventing or treating insulin-resistant type 2 diabetes.

Example 4. Effects of Administration of Combined Preparation of Cyclo-Z and Dapagliflozin on Effects of Lowering Blood Glucose and Regulating Blood Glucose and Content of Glycated Hemoglobin 4-1. Administration of Single and Combined Preparations of Cyclo-Z and Dapagliflozin In order to measure the effects of regulating blood glucose by the combined preparation of Cyclo-Z and dapagliflozin, 6-week-old. KKAy mice were purchased from CLEA Japan, Inc. and reared under predetermined conditions (temperature: 22±2° C., relative humidity: 55±10%, daily cycle: 12 hour). 7 animals were grouped, water and food were freely supplied in cages, and the groups were subjected to acclimatization for 1 week before the experiment and used for the experiment.

After the acclimatization period, the animals were divided into 6 groups, and single and combined preparations of Cyclo-Z and dapagliflozin at weight ratios shown in the following Table 2 were orally administered daily for 10 weeks.

TABLE 2

| Group | Cyclo-Z | Dapagliflozin |
|---|---|---|
| Normal control | — | — |
| Single administration group | 3 | — |
|  | — | 0.02 |
|  | — | 1 |
| Cyclo-Z:Dapagliflozin complex composition administration group | 3 | 0.02 |
|  | 3 | 1 |

4-2. Measurement of Effect of Regulating Blood Glucose in Mice

In order to confirm the effect of regulating blood glucose, the animals in the control and the experimental groups were intraperitoneally injected with 2 g/kg of glucose after fasting for 16 hours, and the blood glucose level was measured at 15, 30, 60, 90, and 120 minutes. A blood glucose strip (GC Pharma Corporation, Gyeonggi Province, Korea) was used to measure blood glucose. An oral glucose tolerance test (OGTT) was used to measure the blood glucose level. For the experimental results, the significance thereof was verified by performing a t-test between the negative control and the experimental groups, and the experimental results exhibited a statistically significant difference (****$p<0.0001$). Further, the significance thereof was verified by performing a t-test between the single administration group and the complex administration group, and the experimental results exhibited a significant difference (#$p<0.05$, ####$p<0.0001$).

Figure 4A:
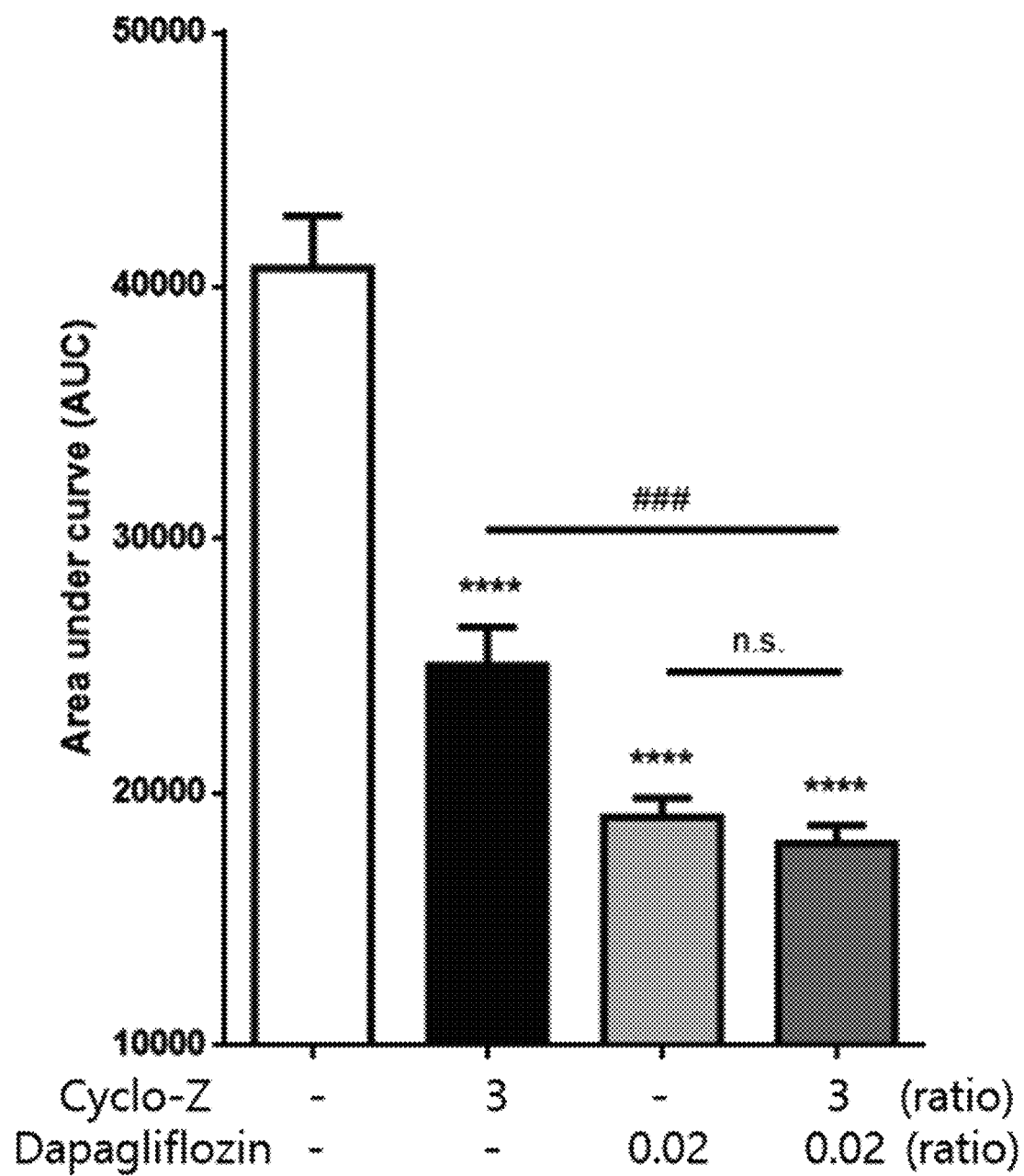
FIGS. 4A to 4D.
Figure 4B:
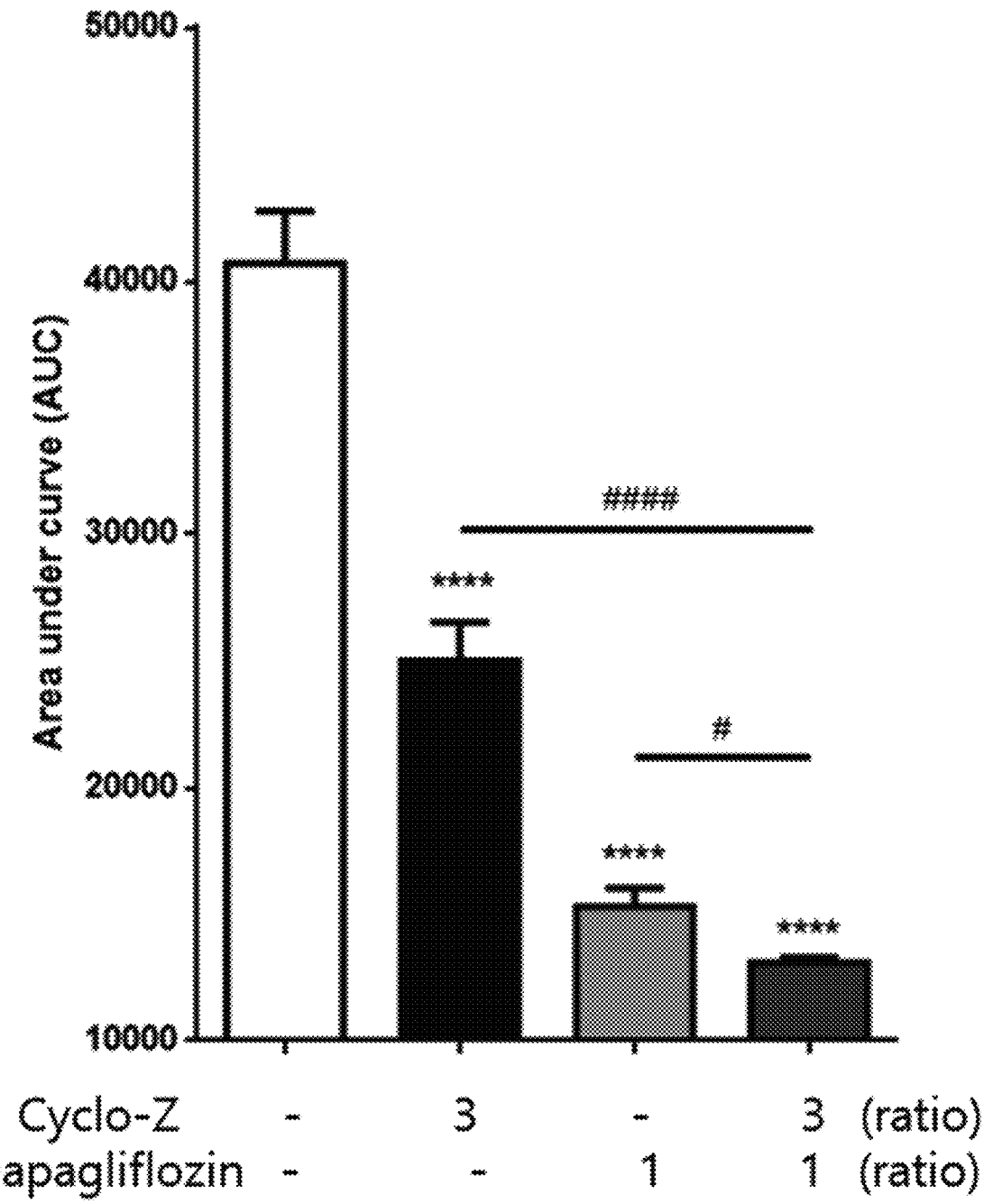

As a result, as illustrated in FIGS. 4A and 4B, it was confirmed that blood glucose was rapidly reduced 2 hours after glucose administration in the complex administration group in which Cyclo-Z and dapagliflozin were administered at a weight ratio of 3:1 rather than at a weight ratio of 3:0.02, compared to the single administration group.

Therefore, since an excellent significant action of reducing the concentration of blood glucose in the combined preparation administration group rather than the case of the Cyclo-Z single or dapagliflozin single administration group was confirmed, it could be seen that the combined preparation in which Cyclo-Z and dapagliflozin were administered at a weight ratio of 3:1 could be usefully used for preventing or treating diabetes, and it could be seen that the combined preparation could be usefully used as an agent for preventing or treating insulin-resistant type 2 diabetes.

4-3. Measurement of Glycated Hemoglobin in Mice

There are various methods for diagnosing diabetes, such as the measurement of blood glucose, but since the measurement of blood glucose is inaccurate due to various factors such as diet and exercise, the measurement of glycated hemoglobin in blood is one of the effective methods in order to manage and treat diabetes. In 1986, the American Diabetes Association began using the amount of glycated hemoglobin which is a relatively stable indicator as a diabetes management indicator by proposing the measurement of glycated hemoglobin twice a year to manage all forms of diabetes. (Korean Patent Application Laid-Open No. 10-2009-0006999, published on Jan. 16, 2009). In the present example, the present inventors intended to examine the contents of glycated hemoglobin in mice after ingestion of a combined preparation of Cyclo-α and dapagliflozin. In order measure the effect of lowering glycated hemoglobin of the combined preparation of Cyclo-Z and dapagliflozin, whole blood was collected from the tail vein of animals in the control and the experimental groups, injected into a Hemoglobin A1 reagent kit, and then glycated hemoglobin content was measured using a DCA vantage analyzer (Siemens, New York, USA). For the experimental results, the significance thereof was verified by performing a t-test between the negative control and the experimental groups, and the experimental results exhibited a significant difference (*$p<0.05$, $p<0.01$, *$p<0.001$, ****$p<0.0001$). Further, the significance thereof was verified by performing a t-test between the single administration group and the complex administration group, and the experimental results exhibited a significant difference (#$p<0.05$, ###$p<0.001$).

Figure 4C:
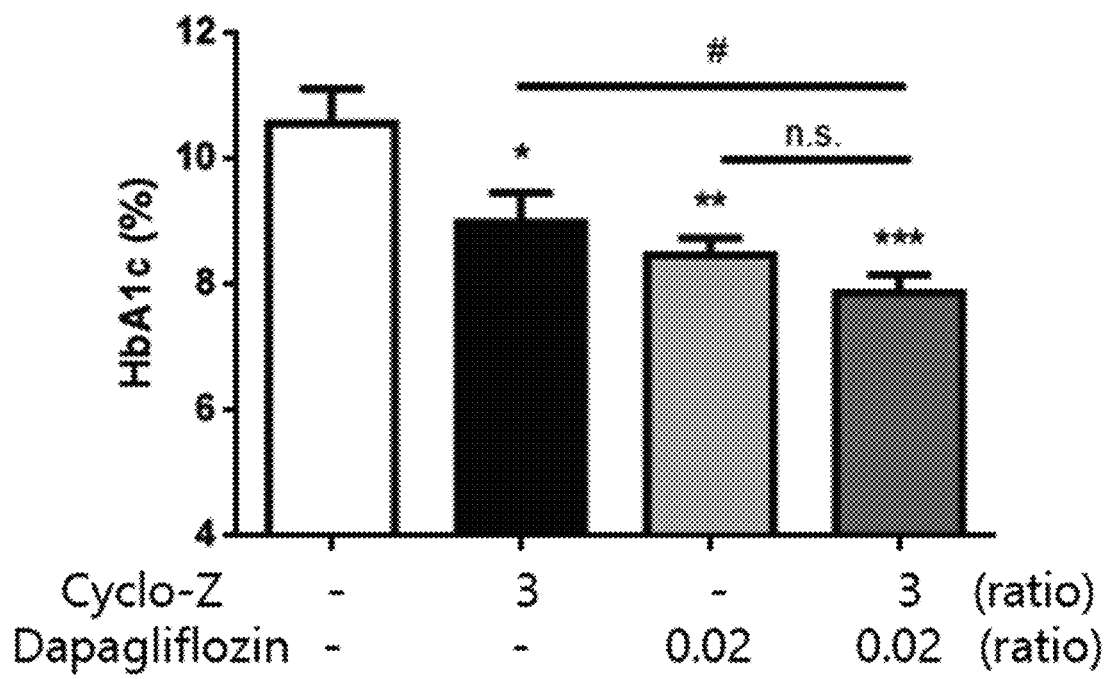
Figure 4D:
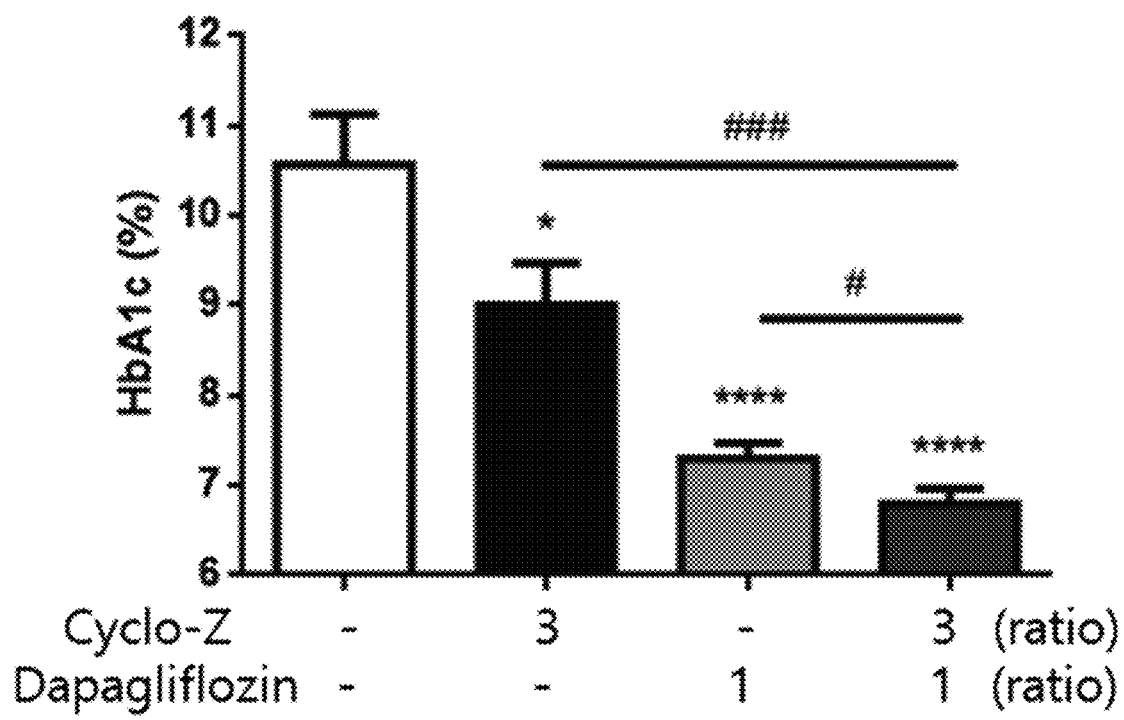

As a result, as illustrated in FIGS. 4C and 4D, it was confirmed with statistical significance that the effect of inhibiting the production of glycated hemoglobin is enhanced in the complex administration group in which Cyclo-Z and dapagliflozin were administered at a weight ratio of 3:1 rather than at a weight ratio of 3:0.02, compared to the single administration group.

Therefore, it could be seen that the combined preparation of Cyclo-Z and dapagliflozin has an effect of reducing glycated hemoglobin, and thus could be usefully used as an agent for preventing or treating insulin-resistant type 2 diabetes.

Comparative Example 1. Measurement of Effect of Regulating, Blood Glucose in Mice by Administration of Combined Preparation of Cyclo-Z and Metformin 1-1. Administration of Single and Combined Preparations of Cyclo-Z and Metformin In order to measure the effects of regulating blood glucose by the combined preparation of Cyclo-Z and metformin, 6-week-old KKAy mice were purchased from CLEA Japan, Inc. and reared under predetermined conditions (temperature: 22±2° C., relative humidity: 55±10%, daily cycle: 12 hour). 8 animals were grouped, water and food were freely supplied in cages, and the groups were subjected to acclimatization for 1 week before the experiment and used for the experiment.

After the acclimatization period, the animals were divided into 8 groups, and single and combined preparations of Cyclo-Z and metformin at weight ratios shown in the following Table 3 were orally administered daily for 8 weeks.

TABLE 3

| Group | Cyclo-Z | Metformin |
| --- | --- | --- |
| Normal control | — | — |
| Single administration group | 1 | — |
| | — | 10 |
| | — | 20 |
| | — | 33.3 |
| Cyclo-Z:Metformin complex composition administration group | 1 | 10 |
| | 1 | 20 |
| | 1 | 33.3 |

1-2. Measurement of Effect of Regulating Blood Glucose in Mice

In order to confirm the effect of regulating blood glucose, the animals in the control and the experimental groups were intraperitoneally injected with 2 g/kg of glucose after fasting for 16 hours, and the blood glucose level was measured at 15, 30, 60, 90, and 120 minutes. An oral glucose tolerance test (OGTT) was used to measure the blood glucose level. For the experimental results, the significance thereof was verified by performing a t-test between the experimental groups and the control, and the experimental results exhibited a significant difference (*$p<0.05$, ***$p<0.0005$).

Figure 5A:
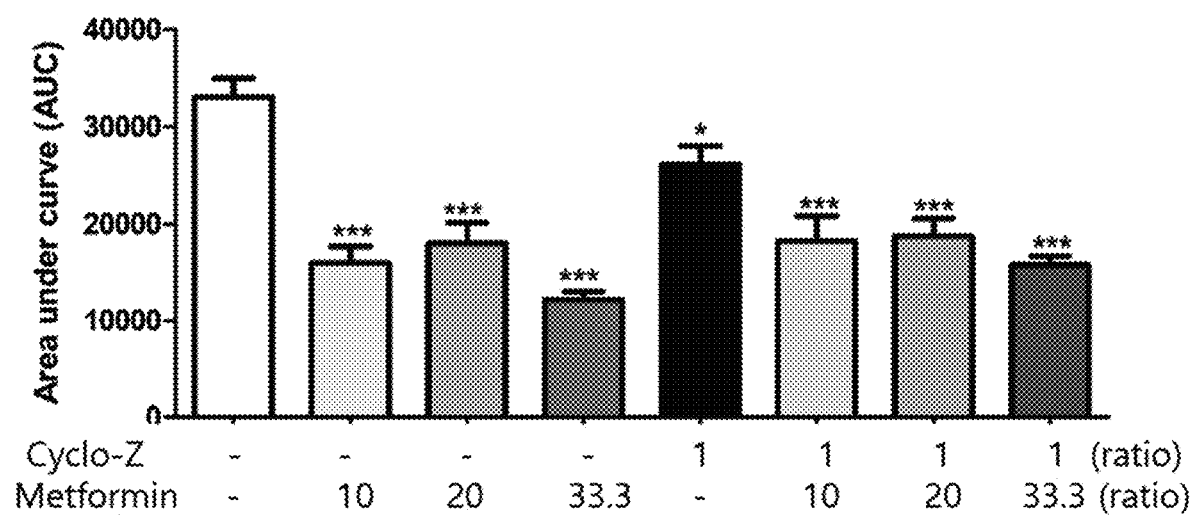
FIGS. 5A and 5B.
Figure 5B:
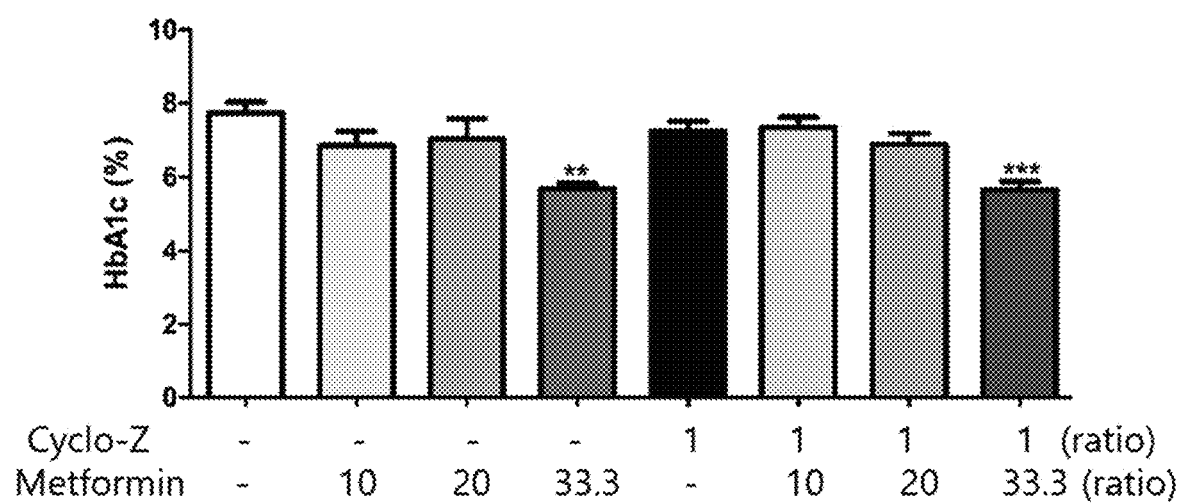

As a result, as illustrated in FIG. 5A, it was confirmed that there was no synergistic effect in any of the experimental groups treated with metformin alone and the combined preparation administration groups.

1-3. Measurement of Glycated Hemoglobin in Mice

In the regulation of blood glucose, not only the blood glucose level, but also the glycated hemoglobin level should be examined together. This is because a 1% reduction in glycated hemoglobin has the effect of reducing diabetes-related complications by more than 20%. In the present example, the present inventors intended to examine the contents of glycated hemoglobin in mice after ingestion of a combined preparation of Cyclo-α and metformin. In order to measure the effect of lowering glycated hemoglobin of the combined preparation of metformin and Cyclo-Z, whole blood was collected from the tail vein of animals in the control and the experimental groups, injected into a Hemoglobin A1 reagent kit, and then glycated hemoglobin content was measured using a DCA vantage analyzer (Siemens, New York, USA). For the experimental results, the significance thereof was verified by performing a t-test between the experimental groups and the control, and the experimental results exhibited a significant difference ($p<0.005$, *$p<0.0005$).

As a result, as illustrated in FIG. 59, it was confirmed that there was no synergistic effect in any of the experimental groups treated with metformin alone and the combined preparation administration groups.

The above-described description of the present invention is provided for illustrative purposes, and the person skilled in the art to which the present invention pertains will understand that the present invention can be easily modified into other specific forms without changing the technical spirit or essential features of the present invention. Therefore, it should be understood that the above-described embodiments are illustrative in all aspects and are not restrictive.

The invention claimed is:

1. A method for treating diabetes in a subject in need thereof, the method comprising orally, intranasally, intravenously, subcutaneously, or intraperitoneally administering to the subject (a) a zinc salt and cyclo-hispro or a pharmaceutically acceptable salt thereof at a weight ratio of the zinc salt to the cyclo-hispro or a pharmaceutically acceptable salt thereof of from 2:1 to 3:1; and (b) an antidiabetic drug selected from the group consisting of (a) an insulin sensitizer selected from the group consisting of rosiglitazone, troglitazone, ciglitazone, pioglitazone, and englitazone; (b) a sodium-glucose co-transporter 2 inhibitor selected from the group consisting of canagliflozin, dapagliflozin, empagliflozin, ipragliflozin, tofogliflozin, luseogliflozin, remogliflozin, remogliflozin etabonate, and ertugliflozin; and (c) a dipeptidyl peptidase-4 inhibitor selected from the group consisting of sitagliptin, linagliptin, vildagliptin, gemigliptin, saxagliptin, alogliptin, teneligliptin, anagliptin, and evogliptin;

wherein the zinc salt and the cyclo-hispro or a pharmaceutically acceptable salt thereof is administered simultaneously, separately or sequentially with the antidiabetic drug; and wherein a weight ratio of the zinc salt and the cyclo-hispro or a pharmaceutically acceptable salt thereof to the insulin sensitizer is 1:2; a weight ratio of the zinc salt and the cyclo-hispro or a pharmaceutically acceptable salt thereof to the sodium-glucose co-transporter 2 inhibitor is from 3:0.02 to 3:1; and a weight ratio of the zinc salt and the cyclo-hispro or a pharmaceutically acceptable salt thereof to the dipeptidyl peptidase-4 inhibitor is 3:2.

2. The method of claim 1, wherein the diabetes is type 2 diabetes.

3. The method of claim 1, wherein the treatment of diabetes is caused by the ability to absorb glucose, to lower blood glucose, to regulate blood glucose, or to inhibit the production of glycated hemoglobin.

4. The method of claim 1, wherein the weight ratio of the zinc salt and the cyclo-hispro or a pharmaceutically acceptable salt thereof to the insulin sensitizer is 1:2.

5. The method of claim 1, wherein the weight ratio of the zinc salt and the cyclo-hispro or a pharmaceutically acceptable salt thereof to the sodium-glucose co-transporter 2 inhibitor is from 3:0.02 to 3:1.

6. The method of claim 1, wherein the weight ratio of the zinc salt and the cyclo-hispro or a pharmaceutically acceptable salt thereof to the dipeptidyl peptidase-4 inhibitor is 3:2.

* * * * *